(12) United States Patent
Moyers

(10) Patent No.: US 7,073,508 B2
(45) Date of Patent: Jul. 11, 2006

(54) METHOD AND DEVICE FOR REGISTRATION AND IMMOBILIZATION

(75) Inventor: Michael F. Moyers, Colton, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 51 days.

(21) Appl. No.: 10/965,704

(22) Filed: Oct. 13, 2004

(65) Prior Publication Data

US 2005/0284490 A1    Dec. 29, 2005

Related U.S. Application Data

(60) Provisional application No. 60/614,158, filed on Sep. 29, 2004, provisional application No. 60/583,063, filed on Jun. 25, 2004.

(51) Int. Cl.
*A61F 11/00* (2006.01)

(52) U.S. Cl. .................. 128/857; 128/869; 128/870

(58) Field of Classification Search ............. 128/845, 128/846, 857, 858, 869, 870; 606/130
See application file for complete search history.

(56) References Cited

U.S. PATENT DOCUMENTS

| | | | |
|---|---|---|---|
| 3,545,739 A | 12/1970 | D'Avignon |
| 3,640,787 A | 2/1972 | Heller |
| 3,745,998 A | 7/1973 | Rose |
| 3,762,404 A | 10/1973 | Sakita |
| 3,778,049 A | 12/1973 | Viamonte, Jr. |
| 3,851,644 A | 12/1974 | Slagle |
| 3,897,345 A | 7/1975 | Foster |
| 3,897,777 A | 8/1975 | Morrison |
| 4,064,401 A | 12/1977 | Marden |
| 4,256,112 A | 3/1981 | Kopf et al. |
| 4,327,046 A | 4/1982 | Davis et al. |
| 4,347,213 A | 8/1982 | Rogers, Jr. |
| 4,400,820 A | 8/1983 | O'Dell et al. |
| 4,450,122 A | 5/1984 | Gallina |
| 4,504,050 A | 3/1985 | Osborne |
| 4,550,713 A | 11/1985 | Hyman |
| 4,616,814 A | 10/1986 | Harwood-Nash et al. |
| 4,752,064 A | 6/1988 | Voss |
| 4,979,519 A | 12/1990 | Chavarria et al. |
| 5,081,665 A | 1/1992 | Kostich |
| 5,168,514 A | 12/1992 | Horton, Jr. et al. |
| 5,207,688 A | 5/1993 | Carol |
| 5,242,455 A | 9/1993 | Skeens et al. |
| 5,281,232 A | 1/1994 | Hamilton et al. |
| 5,287,576 A | 2/1994 | Fraser |
| 5,361,765 A | 11/1994 | Herlihy et al. |
| 5,370,117 A | 12/1994 | McLaurin, Jr. |

(Continued)

*Primary Examiner*—Henry Bennett
*Assistant Examiner*—Camtu Nguyen
(74) *Attorney, Agent, or Firm*—Knobbe, Martens, Olson & Bear LLP

(57) ABSTRACT

Support devices and pods for the head and neck region of patients undergoing radiation therapy are provided herein. The pod generally includes a support shell shaped to generally conform to the shape of the head and neck region of the patient, a foam insert that conforms to the head and neck region of the patient, and an immobilization facemask attached directly to the shell, thereby facilitating close placement of the radiation beam delivery device to the patient and reducing any attenuation and perturbation of radiation doses directed at the patient. The components of the pod are made from materials having properties that reduce any attenuation and perturbation of prescribed radiation doses.

21 Claims, 5 Drawing Sheets

U.S. PATENT DOCUMENTS

| | | |
|---|---|---|
| 5,370,118 A | 12/1994 | Vij et al. |
| 5,380,336 A | 1/1995 | Misko et al. |
| 5,388,580 A | 2/1995 | Sullivan et al. |
| 5,454,993 A | 10/1995 | Kostich |
| 5,464,411 A | 11/1995 | Schulte et al. |
| 5,531,229 A | 7/1996 | Dean et al. |
| 5,566,681 A | 10/1996 | Manwaring et al. |
| 5,595,191 A | 1/1997 | Kirk |
| 5,771,512 A | 6/1998 | Kurakake et al. |
| 5,775,337 A | 7/1998 | Hauger et al. |
| 5,806,116 A | 9/1998 | Oliver et al. |
| 5,832,550 A | 11/1998 | Hauger et al. |
| 5,848,449 A | 12/1998 | Hauger et al. |
| 5,851,182 A | 12/1998 | Sahadevan |
| 5,947,981 A | 9/1999 | Cosman |
| 5,983,424 A | 11/1999 | Näslund |
| 6,161,237 A | 12/2000 | Tang et al. |
| 6,282,739 B1 | 9/2001 | Livingston |
| 6,308,353 B1 | 10/2001 | Van Steenburg |
| 6,376,846 B1 | 4/2002 | Livingston |
| 6,565,577 B1 | 5/2003 | Cosman |
| 6,698,045 B1 | 3/2004 | Coppens et al. |
| 6,704,957 B1 | 3/2004 | Rhodes |
| 2002/0032378 A1 | 3/2002 | Henderson et al. |
| 2002/0095730 A1 | 7/2002 | Al-Kassim et al. |
| 2002/0120986 A1 | 9/2002 | Erbel et al. |

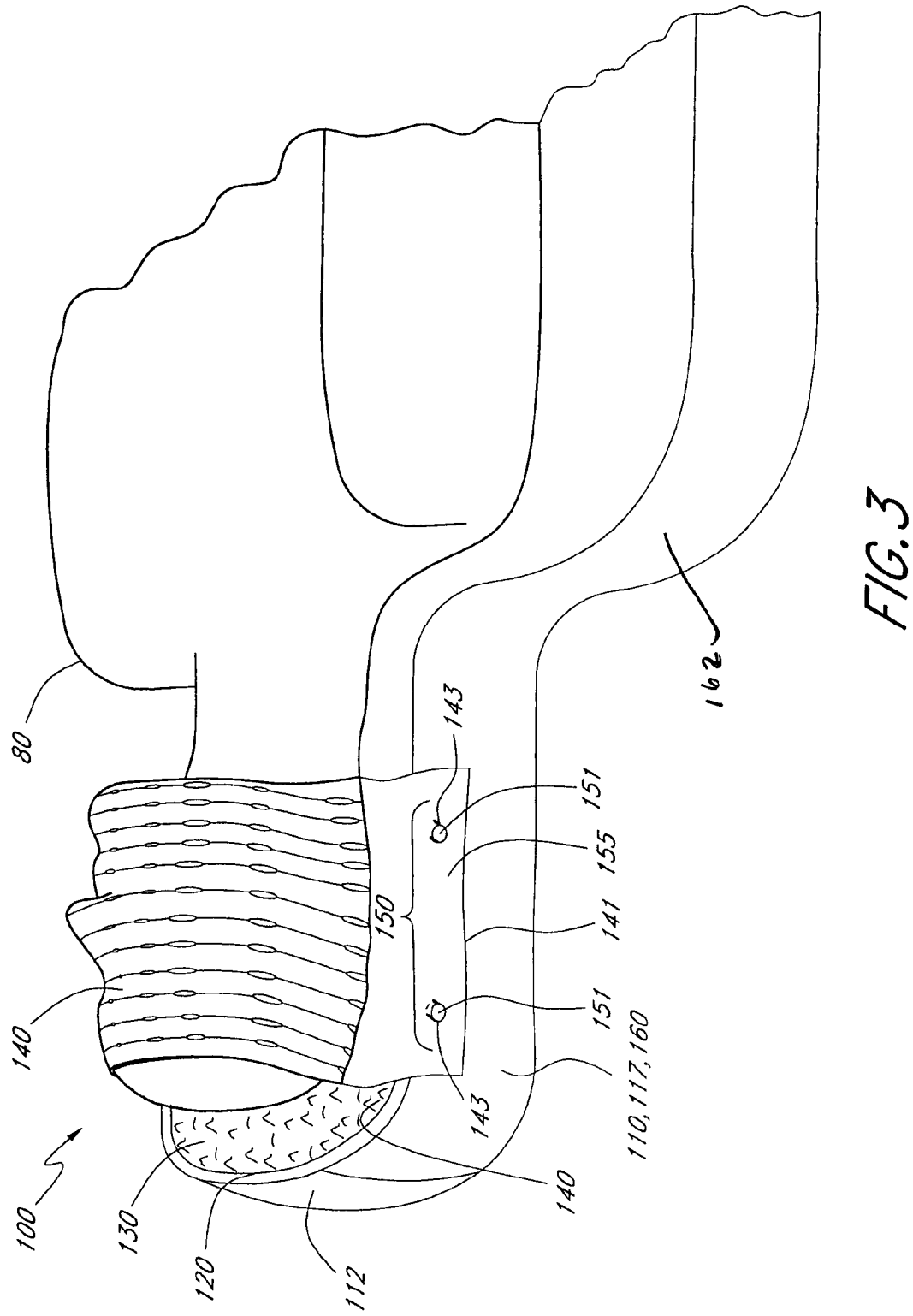

METHOD AND DEVICE FOR REGISTRATION AND IMMOBILIZATION

RELATED APPLICATIONS

This application claims priority to U.S. Provisional Application No. 60/583,063, filed Jun. 25, 2004, titled METHOD AND DEVICE FOR REGISTRATION AND IMMOBILIZATION, and to U.S. Provisional Application No. 60/614,158, filed Sep. 29, 2004, titled METHOD AND DEVICE FOR REGISTRATION AND IMMOBILIZATION, the contents of each of which are hereby incorporated in their entirety into this disclosure by reference.

STATEMENT REGARDING FEDERALLY SPONSORED RESEARCH OR DEVELOPMENT

This invention was made with United States Government support under Cooperative Agreement Number DAMD17-97-2-7016 with the National Medical Technology Testbed, Inc., United States Department of the Army. The United States Government has certain rights in this invention.

BACKGROUND OF THE INVENTION

1. Field of the Invention

The present invention relates to a registration and immobilization device for radiation therapy, and more particularly to a support device that facilitates the delivery of radiation beams from many locations and directions, and that reduces the attenuation and perturbation of radiation beams directed at the patient.

2. Description of the Related Art

Today, approximately 60% of all patients treated for cancer in the United States receive some form of radiotherapy during their course of treatment. An increasing number of patients with nonmalignant diseases also receive treatment with radiation. Examples of these diseases include arteriovenous malformations, macular degeneration, and Parkinson's disease. Radiation treatments have involved the delivery of x-rays or electrons, as well as proton or heavier ion beams. One advantage of protons and heavier ions is the precise nature in which the energy from these particles can be deposited into a patient.

For a typical treatment procedure involving the delivery of ionizing radiation, multiple beams enter the patient at different locations and from different directions. During treatment, the patient is typically placed at one or more designated locations on a patient positioner utilizing a registration device. The patient is typically immobilized with additional devices to maintain alignment of the radiation beam to the diseased target while missing critical normal tissues. Current registration and immobilization devices limit the optimization of beam entry locations and directions because they perturb the radiation beam and cause regions of the patient to receive more or less dose than prescribed. There exists a need for registration and immobilization devices that reduce perturbations in the radiation fields to acceptable levels from the desired entry directions without raising the cost of treatments prohibitively.

When a radiation treatment for a patient is designed, the dose (energy deposited per unit of mass) to non-target tissues is reduced by directing beams of radiation into the patient from multiple directions. This technique spreads the non-target dose over a large volume so that no tissue receives a large dose and critical structures receive extremely low doses. The delineation of target tissues from normal tissues and the selection of beam directions is performed with the assistance of a computerized treatment planning system (TPS). Necessary input information to the TPS can include patient images from x-ray axial computed tomography (CT). Magnetic resonance imaging (MRI) and nuclear medicine studies such as PET are also helpful in separating the diseased and normal tissues. Output from the TPS includes beam directions, shape of normal tissue shields (collimators) for each beam, and alignment information for each beam.

The patient alignment process typically comprises five separate tasks:

1. Registration—The patient is placed on a patient positioner (PP) in a reproducible manner.
2. Immobilization—The registered patient is fixated and attached to the PP so that they move together as a single unit in a controlled fashion.
3. Localization—The location of the target relative to the diagnostic, simulation, or treatment unit is determined. Typically, this is done by radiographic triangulation.
4. Positioning—The PP is moved to place the target in the desired orientation at the desired location.
5. Verification—The patient's orientation and location are verified. The technique used for this task may or may not be the same technique used for localization.

Any of these five tasks may require iteration to succeed. When proper alignment is maintained, the margin placed around the target to account for motion can be reduced, dose to diseased tissue increased, and dose to critical tissues reduced, which in turn results in higher probability of cure with fewer complications.

Improved registration can be achieved using devices customized to the individual patient. Low-density polystyrene (e.g., Styrofoam®) has occasionally been cut to match the patient contours but this is a labor intensive procedure and is not commonly used. A faster system that is commercially available is a vinyl bag filled with polystyrene beads. The patient lies on the bag and a vacuum applied inside the bag. Once all the air is removed, the result is a hard cast of the patient. Although the beads in the bag are minimally perturbing themselves, the thick surrounding bag can perturb the beam along its edges and folds similarly to the headrest supports. The possibility of vacuum leaks is another concern with the bead bags. Yet another concern is that contamination by bodily fluids be thoroughly cleaned between patients.

After registration of a head and neck patient to the PP, the head is immobilized. This is typically accomplished with a net that covers the patient and registration device and attaches to the PP. The net is usually a sheet of the thermoplastic polyepsilon-caprolactone that has been perforated with a defined hole pattern. This plastic, with a chemical composition $((CH_2)_5CO_2)_n$, becomes soft between temperatures of about 140° F. to about 180° F. and can be draped over the patient for molding to the patient's contours. The plastic will bind to itself when warm or with toluene or methyl chloride when cold. After cooling, the material becomes hard and takes on the shape of the patient. When stretched over the face and shoulders, the small holes in the sheet become large enough that the patient can breath without restriction. The finished device is often called a facemask or mask.

One major problem with masks is how to attach them to either the registration device or the PP. This is done in a secure manner such that: 1) the patient and PP move as a single unit, 2) the patient can not move during treatment, and 3) the patient is able to quickly release themselves if there is an emergency. The mask material is typically held in place between the two plastic blocks by a plurality of screws threaded through holes in both the top and bottom pieces and the thermoplastic. The frame is attached to the tabletop of the PP using cam style clamps. By reaching up and rotating the cam clamps, the ambulatory patient can perform unassisted egress. Unfortunately, this sturdy mask frame places a large block of material completely around the patient at a plane just posterior to the head. The large step in integral thickness that would be seen by radiation beams entering obliquely from below prevents the use of many desired entry angles. Some manufacturers have reduced the thickness of the frame by using thin support plates permanently bonded to the mask material using either glue or ultrasonic welding. These methods necessarily make the support plates disposable and more costly. Even these thinner support plates are often perturbing for proton and electron beams.

The table top and facemask frame also require large skin-to-aperture distances, resulting in large lateral penumbras. If a beam intercepts part of a facemask frame or tabletop, a large perturbation in the dose distribution occurs. Further, the frame and facemask attachment mechanisms prevent entry of radiation beams from a full $3\pi$ direction.

The patient positioners used in radiotherapy that the registration and immobilization devices are attached to have historically had flat tabletops for the patient to lie on. During the 1970s, some table tops were fashioned out of materials with low x-ray attenuation factors. Some table tops also had removable sections or sections with a net which allowed x-ray beams to pass relatively unimpeded to the patient. Unfortunately, the edges of these tabletops cause perturbations to the dose distributions within patients delivered by proton or electron beams. "Pod like" devices have been devised to register and immobilize the whole body of patient for various procedures. These devices contain the patient's body within the scanning region of a XCT scanner, allow beams to enter the patient with near perpendicular incidence, and decrease the need for a flat table top support through which a treatment beam passes. However, none of the devices described above have been optimized to reduce perturbations to the radiation beams nor have they had mask materials affixed directly to them.

SUMMARY OF THE INVENTION

In accordance with one aspect of the embodiments described herein, there is provided a support device for the head and neck region of patients undergoing radiation therapy, such as, for example, treatment with protons, x-rays, gamma rays, etc. The head-and-neck support device is typically mounted onto a table or a whole-body support device, which can be attached to a patient positioning system, such as, for example, a robotic arm or a manually adjustable table or couch. In one embodiment, the head-and-neck support device comprises a pod that comprises a support shell, a facemask, and a facemask-to-shell attachment system. The support device typically further comprises a pod liner and/or a foam insert.

In accordance with another aspect of the embodiments described herein, the head-and-neck support device is designed to reduce the attenuation or distortion of radiation beams directed at the patient. The materials for the various elements of the head-and-neck support device or pod are chosen to minimally perturb or attenuate the intensity of radiation beams directed at the patient. The chosen materials for the pod preferably make the pod compatible x-rays, magnetic resonance imaging (MRI), positron emission tomography (PET), proton beams, electron beams, etc. For example, suitable materials for the shell include Spectra® (a polyethylene fiber), Kevlar® (an aramid fiber), fiberglass, or the like. The materials for the shell are preferably physically thin, yet strong enough to provide cantilevered support for the head and neck region of the patient. The materials for the shell typically have low atomic numbers (e.g., chains of Hydrogen and Carbon, such as, for example, Spectra® or the like) to minimally perturb radiation beams.

In accordance with another aspect of the embodiments described herein, the facemask is attached to the shell in a manner which reduces the attenuation of radiation beams directed at treatment sites within the patient. In one embodiment, the facemask is attached to the lateral regions of the shell with one or more locating pins and/or hook-and-fiber systems, where the pins and the hook-and-fiber systems are also made from materials having low atomic numbers. This is a vast improvement over the existing practice of attaching the facemask to a table-top or other bulky attachment surface, which can result in the perturbation of radiation beams. Another problem associated with bulky facemask attachment surfaces is that beam delivery devices (e.g., the nozzle of the radiation beam source) are prevented from being placed close to the patient's skin. The pods described herein utilize a reduced number of attachment mechanisms (e.g., the pins and/or hook-and-fiber systems) directly between the shell and the facemask to reduce the perturbation of radiation beams, and thereby facilitate close placement of the radiation beam delivery nozzle to the patient. Another advantage of the present facemask-to-shell attachment system is that the facemask can be removed quickly by the patient without assistance from other persons in case of an emergency.

In accordance with another aspect of the embodiments described herein, the shell has an inset or tapered structure, relative to the structure to which the pod is attached (e.g., the table or the whole body pod), thereby facilitating close positioning of the beam delivery devices to the treatment sites. The shell of the pod preferably has a changing profile along the caudal to cephalad direction of the patient, thereby allowing beamline devices close approach to the patient's skin.

In one embodiment, the shell is contoured to conform to the shape or outline of the patient's head and neck region. In one embodiment, the shell is custom fitted for the patient's head and neck region. In another embodiment, the shell is dimensioned to accommodate patients of certain classes of shapes and sizes (e.g., small, medium, large, etc.). In still another embodiment, the shell is dimensioned according to an average patient shape or size, and the foam insert is dimensioned to accommodate patients of different shapes or sizes.

In one exemplary embodiment, the shell approximates or generally conforms to the shape of the head and neck region of the patient. The shell extends longitudinally between a caudal end and a cephalad end, and laterally between a right edge and a left edge. The shell defines a channel between the right and left edges, and has an inner surface and an outer surface. In this particular embodiment, the channel is shaped to accommodate the patient's head and neck anatomical regions. An optional pod liner is located above the shell and below a foam insert. The foam insert sits within the channel and is preferably molded to accommodate the patient's unique anatomy. A facemask is located above the foam insert and is attached to the shell to immobilize the patient. The facemask extends laterally between a right edge and a left edge, and is attached directly to the shell via a facemaskto-shell attachment system that comprises one or more locating pins near the shell lateral edges and one or more receiving slots to receive the locating pins. The attachment system optionally comprises one or more hook-and-fiber systems between the shell outer surface and the lateral edges of the facemask.

In one embodiment, certain sections of the right and left edges of the shell are tapered, thereby reducing the amount of material between the patient and the radiation beam delivery device, and also reducing any edge effects associated with the transition between the shell edges and the space above the pod. It will be noted that an abrupt transition or change in the water equivalency between the pod shell and the space above the pod shell lateral edge can result in radiation beams having intensities that are non-uniform or difficult to predict. The effects of any abrupt transitions in the water equivalency in the beam path referred to herein as edge effects. In one exemplary embodiment, the shell narrows laterally (i.e., from the center to the left, or the center to the right) near the cranial or distal portion of the pod.

In accordance with another aspect of the embodiments described herein, the facemask is directly attached to the pod, thereby eliminating the use of devices that attach the facemask to the a table-top far away from the patient's skin and that prevent close approach of beam delivery devices. The facemask-to-shell attachment system is designed to minimally perturb radiation beams (e.g., proton beams, electron beams, megavoltage x-rays, gamma rays, etc.) directed at the patient.

In accordance with another aspect of the embodiments described herein, the head-and-neck support device facilitates registering a patient to a positioner and immobilizing the patient during imaging, treatment simulations, and treatments, while minimally perturbing any radiation used during those procedures. The head-and-neck support device described herein can be cantilevered to allow unrestricted access or exposure to radiation beams during external beam therapy (e.g., treatment involving the delivery of radiation beams from the patient's superior or cephalad side).

In one embodiment, the head-and-neck support device includes: a pod; a pod liner; a foam insert; a patient protection barrier; a head orientation and positioning system; a facemask; a facemask-to-pod attachment mechanisms; and a pod-to-positioner attachment system.

In accordance with another aspect of the embodiments described herein, the materials of the pod comprise a material having an XCT number that lies on the standard XCT number to relative linear stopping power curve for proton and electrons and on the standard XCT number to relative linear attenuation curve for megavoltage x-rays. In one embodiment, the selected composite material of the pod preferably has a low linear attenuation coefficient (e.g., similar to water) for x-rays and enough strength to provide cantilevered support at reduced thicknesses, so that the pod is compatible with the diagnostic energy x-rays. In another embodiment, the pod material is preferably non-conducting in nature, so that the pod is compatible with MRI. In another embodiment, the pod material preferably has a low linear attenuation coefficient (e.g., similar to water) for gamma rays and has enough strength to provide cantilevered support at reduced thicknesses, so that the pod is compatible with positron emission tomography.

In accordance with another aspect of the embodiments described herein, the pod preferably has a radiographical thickness less than about 7 mm of water at locations where treatment beams pass through. In one embodiment, at least one lateral edge of the pod shell has a radiographical thickness less than or about 1 mm of water to minimally perturb the incident radiation beams. In another embodiment, the change in radiographical thickness is less than about 0.5 mm per about 2 mm of distance at locations where treatment beams pass through.

In accordance with another aspect of the embodiments described herein, the selected pod material bends due to any accumulated microfractures when overstressed, thereby preventing the occurrence of a single catastrophic break. The selected material is preferably resistant to damage, thereby allowing multiple and repeated uses with many patients. The selected material is preferably resistant to water or similar cleaning agents used for cleaning between treatments.

In accordance with another aspect of the embodiments described herein, the pod liner has a water equivalent thickness that is less than about 0.3 mm to minimally perturb radiation beams.

In accordance with another aspect of the embodiments described herein, the components of the head-and-device are preferably made from materials having low atomic numbers (e.g., chains of Hydrogen and Carbon, such as, for example, Spectra®) to minimally perturb radiation beams. The fibers of the selected materials preferably do not perturb the dose distribution delivered to the patient, and are preferably not apparent in images of the patient.

In one approach to preparing the head-and-neck support device for registration and/or immobilization of the patient, the approach includes the steps of: forming a patient customized, molded headrest with respect to the pod; immobilizing the patient's head at a prescribed orientation and position while forming the customized headrest; and forming a custom molded facemask while the patient is in the custom headrest and pod.

In accordance with another aspect of the embodiments described herein, the radiation therapy support device can be configured for any anatomical region of the patient. The features of the support device described herein is not necessarily limited for use in the head and neck region. In another embodiment, the support device is dimensioned and configured to provide cantilevered support to the lower and/or middle regions of the patient's anatomy. In still another embodiment, the support device is shaped according to the outline of the patient's whole body and functions as a whole body pod that facilitates the delivery of radiation beams from almost any angle and that reduces the attenuation or perturbation of any radiation beam doses to be delivered to the patient.

BRIEF DESCRIPTION OF THE DRAWINGS

FIG. 3 is a side elevated view of one embodiment of a radiation therapy support device for the head and neck regions.

DETAILED DESCRIPTION OF THE PREFERRED EMBODIMENT

Figure 1:
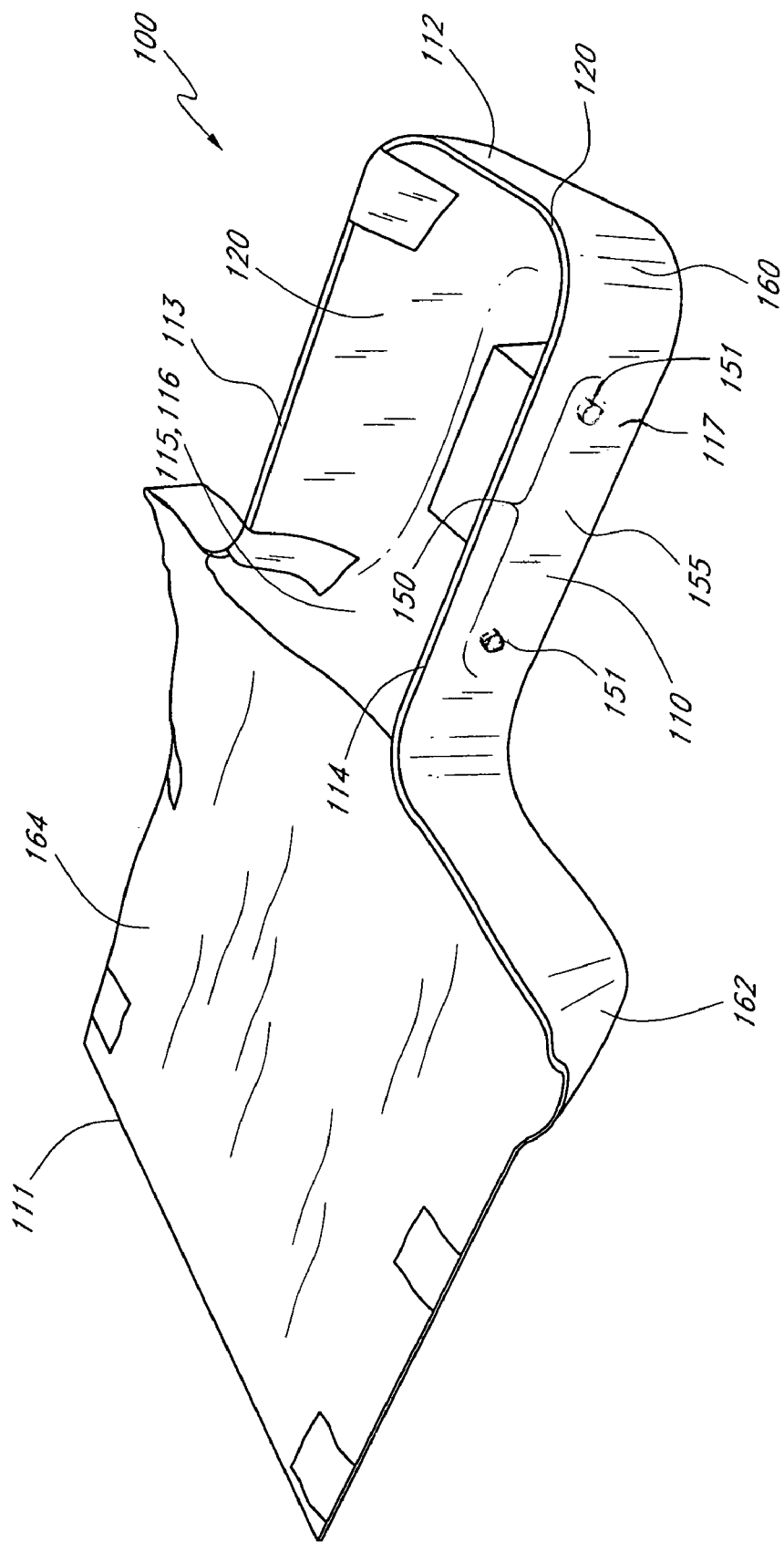
FIG. 1 is a side elevated view of one embodiment of a support shell, a shell liner, and a facemask-to-shell attachment system.

In accordance with one aspect of the embodiments described herein, there is provided a device that facilitates registration and immobilization of patients undergoing radiation treatment without restriction of directions, thereby allowing optimization of the treatment delivery. More specifically, there is provided a support device for the head and neck region of patients undergoing radiation therapy (e.g., treatment with protons, x-rays, gamma rays, etc.). The head-and-neck support device is typically mounted onto one end of a table or a whole-body support device, which is often attached to a patient positioning system (e.g., a robotic arm or a manually adjustable table or couch). The head-and-neck support device generally comprises a support shell, an immobilization device (e.g., a facemask), and a facemask-to-shell attachment system.

In one embodiment, illustrated in FIG. 3, the support device comprises a pod 100 for the head and neck region of the patient 80. The pod 100 comprises: a cantilevered support shell structure 110; an optional pod liner 120; a foam insert 130; a facemask 140; and a facemask-to-shell attachment system 150.

With reference to FIGS. 1 and 2A–C, the support shell 110 approximates or generally conforms to the shape of the head and neck region of the patient 80. The shell 110 extends longitudinally between a caudal end 111 and a cephalad end 112, and laterally between a right edge 113 and a left edge 114. The shell 110 defines a channel 115 between the right and left edges 113, 114. The shell 110 has an inner surface 116 and an outer surface 117. The caudal end 111 of the shell 110 is typically attached to a table or a patient positioner.

The pod liner 120 (optional) is located above the shell 110 and below the foam insert 130. The foam insert or headrest 130 sits within the channel 115 and is molded to accommodate the patient's unique anatomy. The facemask 140 is located above the insert 130 and attached to the shell 110 to immobilize the patient 80. The facemask 140 extends laterally between a right edge 141 and a left edge 142.

The facemask-to-shell attachment system 150 comprises locating pins 151 near the shell lateral edges 113, 114 and receiving slots 143 on the facemask 140 to receive the locating pins 151. The attachment system 150 optionally comprises hook-and-fiber systems 155 between the shell outer surface 117 and the facemask 140 near the lateral edges 141, 142.

Figure 4:
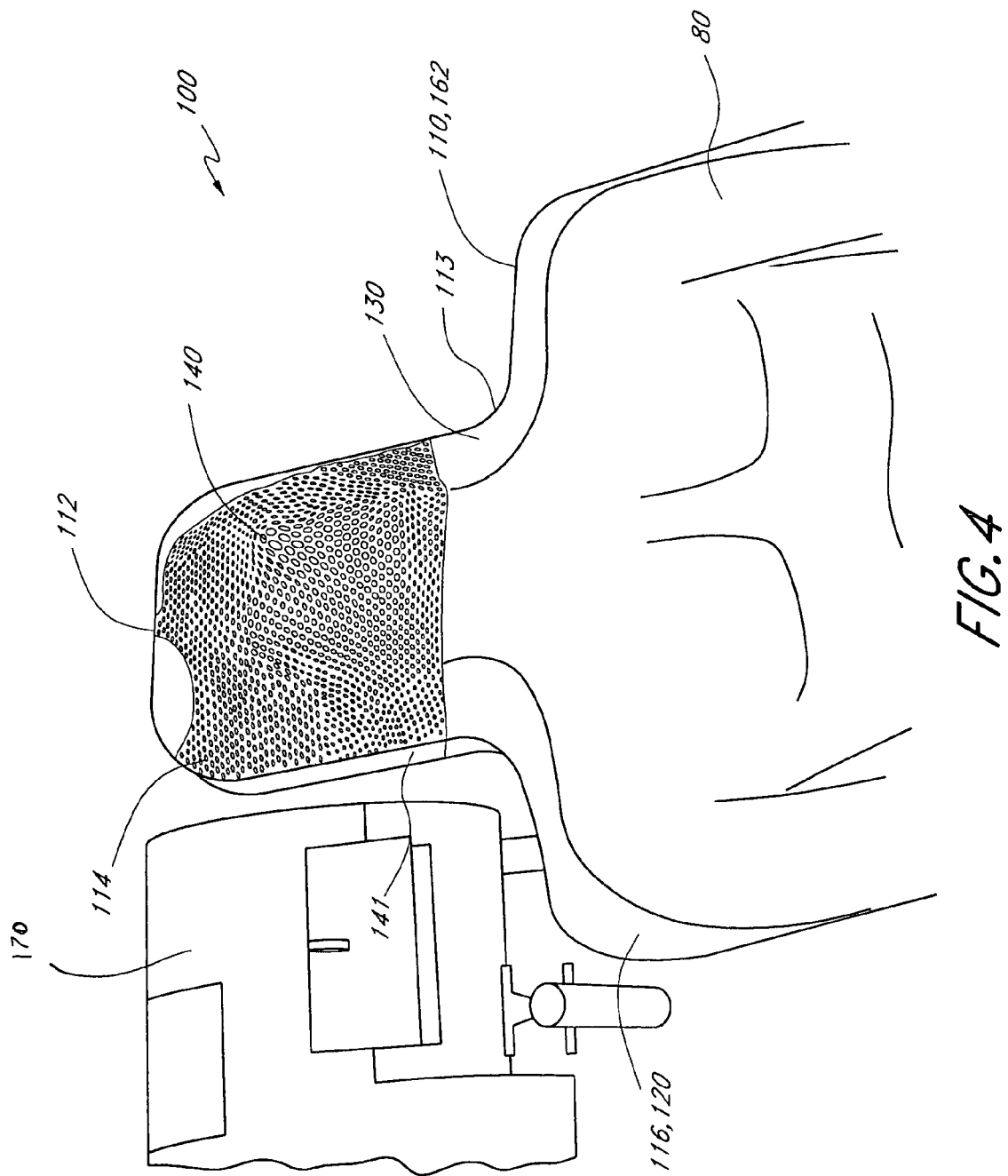
FIG. 4 is an elevated view of the support device of FIG. 3 next to a radiation beam delivery nozzle.

In accordance with one aspect of the embodiments described herein, the support shell 110 is inset or tapered relative to the structure to which the pod 100 is attached. For example, with reference to the embodiment of FIG. 4, the inset of the shell 110 relative to the table or patient positioner facilitates the close positioning of beam delivery devices (e.g., radiation beam nozzle 170) to the patient 80, and therefore more accurate delivery of radiation doses to the treatment sites.

Tapering the pod profiles in transverse, sagittal, and coronal planes reduces the skin-to-aperture distances and therefore the lateral penumbra widths. The thickness of the pod is preferably reduced and tapered at the lateral edges, caudal edge, and cephalad edge, to reduce perturbations in the dose distribution.

Figure 2A:
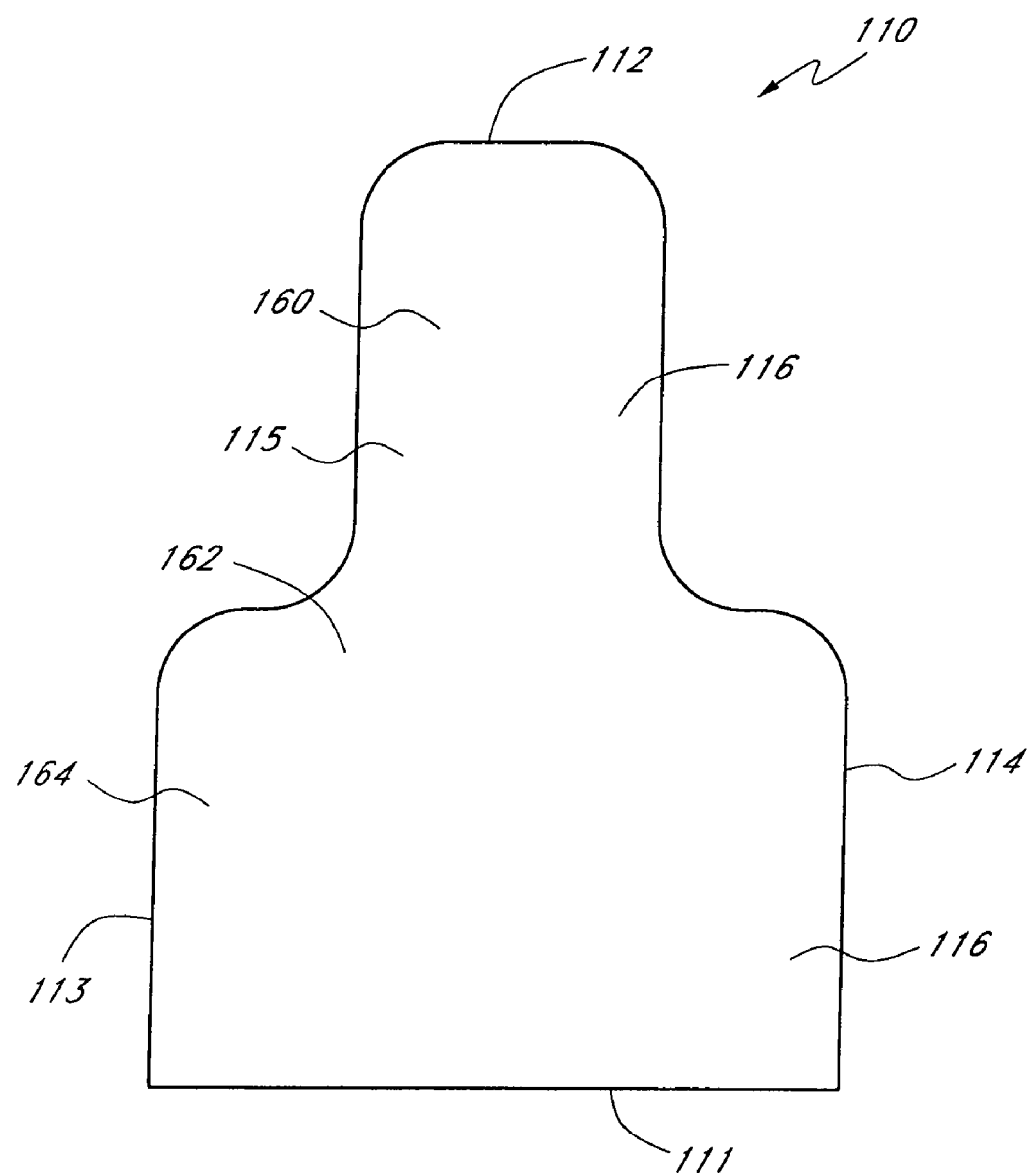
FIG. 2A is a top plan view of one embodiment of a support shell.
Figure 2B:
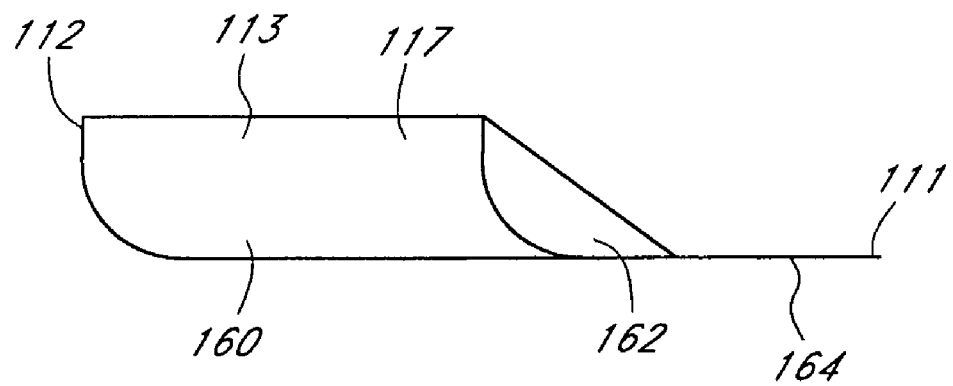
FIG. 2B is a side view of the support shell of FIG. 2A.
Figure 2C:
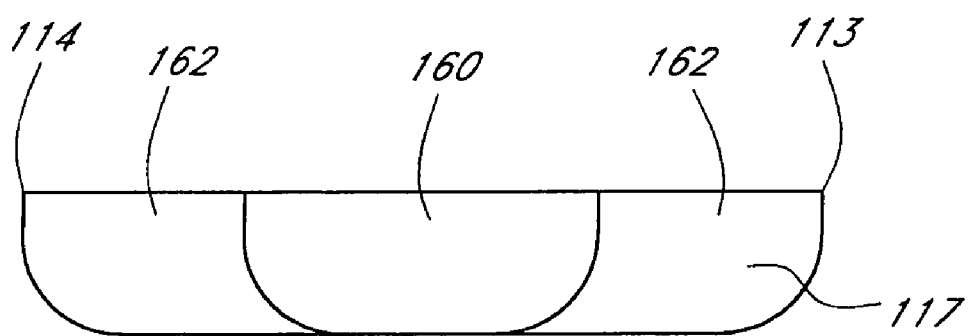
FIG. 2C is a cephalad view of the support shell of FIG. 2A.

With reference to FIGS. 2A–B, in one embodiment, the support shell 110 comprises a head region 160, a shoulder region 164, and a head-to-shoulder transition region 162. Here, the length of the shell 110 (caudal end 111 to cephalad end 112) is about 72 cm, while the length of the head region 160 is about 32 mm. The length of the transition region 162 is about 15 cm, while the length of the shoulder region 164 is about 25 cm. The width of the head region 160 (left lateral edge to right lateral edge) is about 22 mm, while the width of the shoulder region is about 56 cm. For certain radiation treatment protocols, radiation beams of a prescribed intensity are delivered from lateral positions. In certain instances, where the radiation beam traverses one or both of the lateral edges 113, 114, an abrupt transition or change in the water equivalency between the pod shell 110 and the space above the pod shell lateral edges 113, 114 can result in radiation beams having intensities that are non-uniform or difficult to predict. The effects of any abrupt transitions in the water equivalency in the beam path referred to as edge effects. By tapering the lateral edges 113, 114 of the pod 100, edge effects are reduced. In one approach, the lateral edges 113, 114 of the pod are tapered with a gradient from about 0.1 mm water equivalency/mm to about 5 mm water equivalency/mm. In one approach, tapered portion of the lateral edges 113, 114 have a gradient of about 0.5 mm water equivalency/mm. The lateral edges 113, 114 are preferably thin, thereby minimally perturbing any therapeutic proton beams passing through or near any of the lateral edges 113, 114.

In accordance with one aspect of the embodiments described herein, there is provided a facemask-to-shell attachment system 150 that reduces the attenuation or distortion of radiation beams directed at treatment sites within the patient 80. In addition to the material composition of the pod components (discussed in further detail below), another advantage of the pod 100 is the direct attachment or interface between the facemask 140 and the shell 110 to avoid the attenuation radiation beams. Specifically, the facemask 140 is attached to the lateral regions of the shell 110 with one or more locating pins 151 and/or one or more hook-and-fiber systems 155 (e.g., Velcro® or the like).

With reference to FIGS. 1 and 3, in one embodiment, the locating pins 151 are embedded in the support shell 110 and interface with the receiving slots 143 near the lateral edges 141, 142 of the facemask 140 to attach the facemask 140 directly to the shell 110. Here, the attachment system 150 further comprises a hook-and-fiber system 155 on both the left and right edges 141, 142 of the facemask 140. Near the attachment line of the mask 140 to the shell 110, the thermoplastic of the mask 140 preferably has few holes so that the net maintains strength.

The mask 140 can be removed quickly in case of an emergency and does not present any large thickness gradients that will perturb the radiation beam. In another embodiment (not illustrated), the pod 100 has additional pins and quarter turn screws on the bottom surface outside of the treatment and imaging volumes for the purpose of attaching to a patient positioner adapter plate.

The attachment system 150 described herein is an improvement over the existing practice of attaching the facemask to a table-top or other bulky attachment surface that is relatively far away from the patient's skin, thereby preventing the close approach of beam delivery devices. Another problem associated with bulky facemask attachment surfaces is the perturbation of radiation beams. The attachment system 150 utilizes a reduced number of attachment mechanisms (e.g., pins 151) directly between the shell 110 and the facemask 140 to reduce the perturbation of radiation beams. Further, the system 150 allows for quick, unassisted egress by the patient.

In accordance with one aspect of the embodiments described herein, the materials for the various elements of the pod 100 are chosen to minimally perturb or attenuate the intensity of radiation beams directed at the patient 80. The chosen materials for the pod components preferably make the pod 100 compatible with x-rays, magnetic resonance imaging (MRI), positron emission tomography (PET), proton beams, electron beams, etc.

Suitable outer materials for the skin of the shell 110 include polyethylene fibers (e.g., Spectra®), aramid fibers (e.g., Kevlar®), carbon fibers, or the like, or composites thereof. The materials for the shell 110 should be physically thin, yet strong enough to provide cantilevered support for the head and neck regions of the patient 80. The materials for the shell 110 preferably have low atomic numbers (e.g., chains of Hydrogen and Carbon) to minimally perturb radiation beams directed at the patient 80. Suitable core materials of the shell 110 include polymethacrylamides, polyurethane foams, ABS thermoplastics, wood, polystyrene foams, or the like, or composites thereof.

In one embodiment, the shell 110 has a radiographical thickness of less than about 7 mm of water at locations where the radiation beam passes through. In one embodiment, the right shell lateral edge 113 has a radiographical thickness of less than about 1 mm. In one embodiment, left shell lateral edge 114 has a radiographical thickness of less than about 1 mm. In one embodiment, the shell 110 has a radiographical thickness that is less than about 0.5 mm of water per 2 mm of distance at locations where the radiation beam passes through.

Suitable materials for the foam insert 130 for patient registration include polyurethane or other low-density materials that reduce perturbations in the dose distribution due to outscatter. In one approach, a mix of two liquid solutions are used to form a solid, strong, lightweight, polyurethane foam insert 130 that conforms to the contours of the patient 80. For radiation therapy with patients, solution one can be obtained from Dow Chemical Co. as a mix of products "PAPI 20" and "PAPI 27". These products contain polymethylene polyphenyl isocyanate with some diphenylmethane diisocyante. The viscosity of PAPI 20 is about 1800 cps at room temperature while the viscosity of PAPI 27 is about 160 cps. Solution two can also be obtained from Dow as product "Voranol 280". This product contains a polyether polyol, a sucrose/glycerine initiator, and an amine catalyst. The viscosity of Voranol 280 is about 3311 at room temperature. The foam hardens about ten minutes after mixing with a setting temperature of around 112° F. The radiological density of the foam is about 4% of water so that even large thicknesses of foam minimally perturb the beam.

The foam insert 130 should be mechanically stabilized to prevent it from moving and displacing the patient between or during treatments. A geometric shape inserted into the pod design can be used to capture the foam insert 130 at a unique orientation and location. With reference to FIGS. 1 and 2A–C, in one embodiment, the shell 110 defines a channel 115 within which the foam insert 130 is captured or stabilized.

If the shell 110 is to be reusable, the foam insert 130 should be easily removed from the pod 100 without leaving a residue. This can be accomplished several different ways. In one approach, the foam 130 is placed inside a very thin plastic bag. In another approach, the shell 110 is lined with a low-density foam sheet. In yet another approach, the very thin, disposable plastic shell 120 is inserted into the pod before applying the foam chemicals (see FIG. 1). The disposable plastic shells can be massproduced cheaply by vacuum-forming to a negative mold of the inside of the shell 110. In still another approach, the inner surface 116 of the shell 110 is coated with a non-stick chemical or material (e.g., Teflon® or the like).

Suitable materials for the pod liner 120 include plastic, low density foam, or the like, or composite thereof. In one embodiment, the pod liner 120 has a water equivalent thickness that is less than about 0.3 mm.

Suitable materials for the facemask 140 include thermoplastic materials or the like. In one approach, after a patient is "foamed" into the pod 100, the head and neck is immobilized, which is typically accomplished with a net (i.e., the facemask 140) that covers the patient 80 and registration device. The net is typically a sheet of the thermoplastic polyepsilon-caprolactone that has been perforated with a defined, hole pattern. The facemask material is typically manufactured with thicknesses from about 1.6 mm to about 4.8 mm and with varying hole patterns.

In one approach, the sheet of plastic is warmed to a temperature between 140° F. and 180° F. and is then draped over the patient 80 for molding to the patient's contours. When the material cools, it becomes hard acquiring the shape of the patient 80. When stretched over the face and shoulders, the small holes in the sheet become large enough that the patient 80 can breath without restriction. The density of the material is typically about 1.15 g/cm$^3$. A typical finished facemask has a thickness of about 1 mm to about 2 mm alternating with the holes. Although a small perturbation in the dose distribution is produced by the radiation passing by these edges, at most depths these perturbations are blurred and barely measurable. For tumors or critical normal tissues near the surface of the patient 80 these perturbations can be important; in such cases, the mask material can be cut away.

Three characteristics of mask material that effect repeatable patient alignment are heat transfer during initial molding, shrinkage after initial molding, and stiffness. In one approach, a thermoplastic material "Turbocast", marketed by Huestis, is coated with a soft, fleece-like poly-coat. The trapped air acts to insulate the patient's face from the mask material that is heated to above 140° F. for softening prior to molding to the patient 80. The fleece covering also prevents the thermoplastic from sticking to the patient's hair.

Another aspect of the mask material is the perforation pattern. Most materials are made with a regular arrangement of small holes to allow the patient 80 to breath through the nose and mouth and reduce claustrophobia. After the material is stretched around the patient 80, however, the holes get much larger and the mask more resembles a net. Stiffness is then compromised and areas of the patient that change shape rapidly are not sufficiently molded. In one approach, patient alignment accuracy is improved by changing the pattern of holes such that the material is solid (i.e., relatively few or no holes) between the eyes and over the nose and around the chin to better capture the anatomy. The material should also be solid near the attachment point to the pod 100 to provide greater strength. Holes over most of the face should be retained, however, to allow perspiration to evaporate. In another approach, the fit is improved by providing an instant cooling source (e.g., a compressed air nozzle) for rapidly fixing the shape of selected areas molded by hand pressure.

The thermoplastic of the mask 140 preferably has few holes between the eyes and over the nose so there is sufficient molding contact to prevent head rotation. Over the eyes, nostrils, and mouth, the frequency of holes can be much greater to allow free breathing and evaporation of perspiration.

The pins 151 and hook-and-fiber systems 155 are preferably made from materials having low atomic numbers (e.g., chains of hydrogen and carbon), thereby reducing any attenuation or perturbation of radiation beams directed at the patient 80.

Further detail regarding the properties of suitable materials for the pod components are provided in U.S. Provisional Application No. 60/583,063, filed Jun. 25, 2004, titled METHOD AND DEVICE FOR REGISTRATION AND IMMOBILIZATION, and to U.S. Provisional Application No. 60/614,158, filed Sep. 29, 2004, titled METHOD AND DEVICE FOR REGISTRATION AND IMMOBILIZATION, the contents of each of which are incorporated in their entirety into this disclosure by reference. The properties of candidate pod materials examined in these two provisional applications include: the proton linear stopping power; the x-ray linear attenuation coefficient; the XCT number; imaging of fibers within the composite material with a proton beam; imaging of fibers with an x-ray beam; and the perturbation of the proton beam dose distribution in patients produced by edges with various shapes and thicknesses.

In accordance with another aspect of the embodiments described herein, there is provided a support device for the head and neck region of patients undergoing radiation therapy that comprises an orientation device for setting the patient's head angle to the physicians prescription during forming of the foam 130 and preventing the head from rising. In one embodiment, the orientation device comprises a digital protractor located above or near the patient's nose and mouth region.

In accordance with another aspect of the embodiments described herein, there is provided a method of registering and immobilizing a patient for radiation therapy. In one approach, the method generally comprises the steps of: forming a patient customized molded headrest or foam insert; immobilizing the patient's head at a prescribed orientation and position while forming the customized headrest; and forming a custom molded facemask while the patient is in the custom headrest and pod.

While the present invention has been illustrated and described with particularity in terms of certain embodiments, it should be understood that no limitation of the scope of the invention is intended thereby. Features of any of the foregoing methods and devices may be substituted or added into the others, as will be apparent to those of skill in the art. It should also be understood that variations of the particular embodiments described herein incorporating the principles of the present invention will occur to those of ordinary skill in the art and yet be within the scope of the invention.

What is claimed is:

1. A pod for providing radiation treatment to a head and neck region of a patient, the pod comprising:
   a cantilevered support shell shaped to generally conform to the shape of the head and neck region of the patient, the shell extending longitudinally from a shell caudal end to a cephalad end, the shell extending laterally from a first shell lateral edge to a second shell lateral edge, the shell defining a channel between the first and second lateral edges, the shell having a shell inner surface and a shell outer surface, the shell comprising a first material to minimally perturb a radiation beam directed at the patient;
   a pod liner located above the shell inner surface, the liner covering at least a portion of the shell inner surface, the liner made of a second material to minimally perturb the radiation beam;
   a foam insert located above the liner and within the channel, the insert shaped to conform to the head and neck region of the patient, the insert comprising a third material to minimally perturb the radiation beam;
   a facemask located above the insert and attached to the shell to immobilize the patient, the facemask extending laterally between a first facemask lateral edge and a second facemask lateral edge, the facemask comprising a fourth material to minimally perturb the radiation beam; and
   a facemask-to-shell attachment system, the attachment system comprising:
      a first locating pin near the first shell lateral edge, wherein the first locating pin is in communication with the inner and outer surfaces of the shell, wherein the first locating pin comprises a fifth material to minimally perturb the radiation beam; and
      a first receiving slot near the first facemask lateral edge to receive the first locating pin.

2. The pod of claim 1, wherein the facemask-to-shell attachment system further comprises a first hook-and-fiber system between the shell outer surface and the facemask near the first facemask lateral edge.

3. The pod of claim 1, wherein the facemask-to-shell attachment system further comprises:
   a second locating pin near the second shell lateral edge, wherein the second locating pin is in communication with the inner and outer surfaces of the shell, wherein the second locating pin comprises the fifth material; and
   a second receiving slot near the second facemask lateral edge to receive the second locating pin.

4. The pod of claim 3, wherein the facemask-to-shell attachment system further comprises a second hook-and-fiber system between the shell outer surface and the facemask near the second facemask lateral edge.

5. The pod of claim 1, wherein the shell has a radiographical thickness of less than about 7 mm of water at locations where the radiation beam passes through.

6. The pod of claim 1, wherein the first shell lateral edge has a radiographical thickness of less than about 1 mm.

7. The pod of claim 6, wherein the second shell lateral edge has a radiographical thickness of less than about 1 mm.

8. The pod of claim 1, wherein the shell has a radiographical thickness that is less than about 0.5 mm of water per 2 mm of distance at locations where the radiation beam passes through.

9. The pod of claim 1, wherein the pod liner has a water equivalent thickness that is less than about 0.3 mm.

10. The pod of claim 1, wherein the first material comprises a polyethylene fiber.

11. The pod of claim 1, wherein the first material comprises an aramid fiber.

12. The pod of claim 1, wherein the first material comprises a carbon fiber.

13. The pod of claim 1, wherein the first material comprises fiberglass.

14. The pod of claim 1, wherein the first material has an XCT number that lies on a standard XCT number to relative linear stopping power curve for megavoltage x-rays.

15. The pod of claim 1, wherein the second material comprises a plastic.

16. The pod of claim 1, wherein the second material comprises a low density foam.

17. The pod of claim 1, wherein the third material comprises polyurethane.

18. The pod of claim 1, wherein the fourth material comprise a thermoplastic material.

19. The pod of claim 1, wherein the fifth material comprises a polyethylene fiber.

20. The pod of claim 1, wherein the fifth material comprises a plastic.

21. The pod of claim 1, wherein the shell has a radiographical thickness of less than about 7 mm of water at locations where the radiation beam passes through.

* * * * *